United States Patent
Burger

[11] Patent Number: 5,880,698
[45] Date of Patent: Mar. 9, 1999

[54] ARRANGEMENT FOR GENERATING AND TRANSMITTING MICROWAVES, IN PARTICULAR FOR A FILLING LEVEL MEASURING DEVICE

[75] Inventor: Stefan Burger, Freiburg, Germany

[73] Assignee: Endress + Hauser GmbH + Co., Maulburg, Germany

[21] Appl. No.: 874,997

[22] Filed: Jun. 13, 1997

[30] Foreign Application Priority Data

Jul. 23, 1996 [DE] Germany ............ 196 29 593.9

[51] Int. Cl.$^6$ ................................. H01Q 13/00
[52] U.S. Cl. ................... 343/772; 343/786; 333/21 A
[58] Field of Search .................. 343/772, 786, 343/785, 784; 333/21 A, 21 R, 26, 230, 227, 212

[56] References Cited

U.S. PATENT DOCUMENTS

| | | | |
|---|---|---|---|
| 5,245,353 | 9/1993 | Gould | 343/786 |
| 5,331,332 | 7/1994 | West et al. | 343/772 |

FOREIGN PATENT DOCUMENTS

| | | |
|---|---|---|
| 27 44 841 | 10/1977 | Germany . |
| 31 29 425 | 7/1981 | Germany . |
| G 93 12 251 | 8/1993 | Germany . |
| 44 05 855 | 2/1994 | Germany . |
| G 94 12 243 | 7/1994 | Germany . |
| 44 43 055 | 12/1994 | Germany . |
| 1600668 | 10/1977 | United Kingdom . |

OTHER PUBLICATIONS

Ragan, George L. *Microwave Transmission Circuits*, 1948, pp. 314–361.
Panzke, Rolf. *Beruhrungslose kontinuierliche Fullstandsmessung mit Mikrowellen*, 1990, pp. 181–184.

*Primary Examiner*—Don Wong
*Assistant Examiner*—Hoang Nguyen
*Attorney, Agent, or Firm*—Bose McKinney & Evans

[57] ABSTRACT

An arrangement is provided for generating and transmitting microwaves, in particular for a filling level measuring device, which arrangement generates a microwave mode which has a radiation characteristic with a pronounced forward lobe and which arrangement can be used in a large frequency range. It comprises a microwave generator (1), an antenna (2) of circular cross section and a coaxial line (3), which leads from the microwave generator (1) to the antenna (2) and has an inner conductor (31) and an outer conductor (32), and has the feature that on a rear wall (21) of the antenna (2) there is arranged a transmitting wire (5), which runs in the interior of the antenna (2), the first end (51) of which is connected to the inner conductor (31) of the coaxial conductor (3), the second end (52) of which is connected to the rear wall (21) of the antenna (2) and which has a straight portion (53) and legs (54, 55) adjoining the latter.

14 Claims, 5 Drawing Sheets

ARRANGEMENT FOR GENERATING AND TRANSMITTING MICROWAVES, IN PARTICULAR FOR A FILLING LEVEL MEASURING DEVICE

The invention relates to an arrangement for generating and transmitting microwaves, in particular for a filling level measuring device, the arrangement comprising
a microwave generator,
an antenna of circular cross section and
a coaxial line leading from the microwave generator to the antenna, having an inner conductor and an outer conductor.

Arrangements for generating and transmitting microwaves are used, inter alia, in filling level measuring technology. In filling level measurement, microwaves are transmitted by means of an antenna to the surface of a filled product and echo waves reflected at the surface are received. An echo function representing the echo amplitudes as a function of the distance is formed and used to determine the probable useful echo and its delay. The delay is used to determine the distance between the surface of the filled product and the antenna.

All known methods which make it possible to measure relatively short distances by means of reflected microwaves can be used. The most well-known examples are pulse radar and frequency modulation continuous wave radar (FMCW radar).

In the case of pulse radar, short microwave transmission pulses, referred to hereafter as wave packets, are periodically transmitted, reflected from the surface of the filled product and received again after a distance-dependent delay. The received signal amplitude, as a function of time, represents the echo function. Each value of this echo function corresponds to the amplitude of an echo reflected at a certain distance from the antenna.

In the case of the FMCW method, a continuous microwave which is periodically linearly frequency-modulated, for example in accordance with a sawtooth function, is transmitted. In comparison with the instantaneous frequency, which the transmitted signal has at the time of reception, the frequency of the received echo signal therefore has a frequency difference which depends on the delay of the echo signal. The frequency difference between the transmitted signal and the received signal, which can be obtained by mixing the two signals and evaluating the Fourier spectrum of the mixed signal, consequently corresponds to the distance of the reflecting surface from the antenna. Furthermore, the amplitudes of the spectral lines of the frequency spectrum obtained by Fourier transformation correspond to the echo amplitudes. This Fourier spectrum therefore in this case represents the echo function.

Electromagnetic waves propagate in coaxial lines in transversal-electro-magnetic mode (TEM mode) without any dispersion. This field mode is therefore particularly well suited for transporting wave packets or electromagnetic waves of which the frequencies have one bandwidth. The advantage of dispersion-free propagation is important in particular whenever the frequencies of the waves or wave packets to be transmitted have the desired bandwidth. Wave packets fed in then experience virtually no widening, and in the case of linearly frequency-modulated microwaves a linearity deviation is largely avoided.

However, for the directed transmission of electromagnetic waves by means of an antenna, those modes which have a radiation characteristic with a pronounced forward lobe are better suited. This is a property of the transversal-electrical 11 mode (TE-11), capable of propagation in circular waveguides. Therefore, a mode conversion has to be performed, in order that the major component of the microwave energy generated is transmitted in the desired direction.

Depending on the dimensions of a circular waveguide, here the antenna, there is a frequency range in which the TE-11 mode is the only mode capable of propagation. Above this frequency range, even higher modes, less well suited for the directed transmission of microwaves, for Example the TM-01 mode, are also capable of propagation.

In DE-A 27 44 841 there is described an arrangement for generating and transmitting microwaves which comprises
a microwave generator,
an antenna and
a coaxial line, leading from the microwave generator to the antenna, having an inner conductor and an outer conductor.

The antenna has an entry opening of rectangular cross section. In this portion of the antenna, which in terms of its geometry is a short-circuited rectangular waveguide, there is a transmitting mushroom, connected to the coaxial line, arranged for example in a rear wall closing off the antenna. Adjoining the rectangular waveguide is an adapter, by which the rectangular cross section is continuously transformed into a circular cross section. Adjoining the adapter is a portion of antenna of an essentially exponentially widening circular cross section.

The rectangular waveguide is to be dimensioned for a desired frequency range in such a way that virtually only the transversal-electrical 10 mode (TE-10 mode) is capable of propagation and higher modes experience a strong attenuation. In the adapter, the TE-10 mode of the rectangular waveguide changes into the TE-11 mode of the circular waveguide.

In DE-A 27 44 841 it is specified that this arrangement can be used in the case of filling level measuring devices.

A disadvantage of such an arrangement is that the mechanical production of the adapter is complex. A further disadvantage is that two additional transitions are provided, to be specific from the coaxial conductor to the rectangular waveguide and from the rectangular waveguide to the portion of circular cross section, power losses occurring at each of the transitions on account of sudden changes in impedance.

Furthermore, it is customary to arrange the transmitting mushroom directly on a circular waveguide which is closed off at one end. For inducing the desired TE-11 mode, it is necessary here to introduce the transmitting mushroom laterally into the circular waveguide and not through the rear wall closing off the circular waveguide.

One disadvantage of such an arrangement is that the lateral attachment of the transmitting mushroom generally necessitates an additional housing for protecting the coaxial line connected to the mushroom, and the diameter of the arrangement is consequently increased in comparison with an arrangement in which the coupling in of the microwaves takes place through a rear wall of the antenna.

A further disadvantage is that, on account of the asymmetry of the arrangement, not only the TE-11 mode, but also higher modes are induced. Higher modes have, however, a radiation characteristic with a larger aperture angle and are therefore less well suited for directed transmission. The frequency range in which essentially only the TE-11 mode is capable of propagation is smaller in a circular waveguide than the frequency range in which essentially only the TE-10 mode is capable of propagation in a rectangular waveguide.

It is an object of the invention to specify an arrangement for generating and transmitting microwaves, in particular for a filling level measuring device, which generates a microwave mode which has a radiation characteristic with a pronounced forward lobe, and which can be used in a large frequency range.

Furthermore, it is an object of the invention to specify an arrangement for generating and transmitting microwaves, in particular for a filling level measuring device, which can be used within a frequency range which is greater than the frequency range in which the desired microwave mode with the radiation characteristic which has a pronounced forward lobe is the only mode capable of propagation, and in which nevertheless only the desired mode is generated and transmitted.

The invention achieves this by there being fastened on a rear wall of the antenna a transmitting wire, which runs in the interior of the antenna, the first end of which is connected to the inner conductor of the coaxial conductor, the second end of which is connected to the rear wall of the antenna and which has a straight portion and two legs adjoining the latter.

According to one embodiment of the invention, the straight portion of the transmitting wire runs at a distance from the rear wall of the antenna, and the distance between he antenna and two legs of the transmitting wire, which are bounded by the ends and the portion, increases with increasing distance from the rear wall of the antenna.

According to a further embodiment, the average distance between the straight portion of the transmitting wire and the rear wall of the antenna is equal to one quarter of the waveguide wavelength in the antenna at a frequency to be transmitted, in particular at a center frequency of a frequency spectrum of a microwave transmission pulse to be transmitted or at a center frequency of a linearly frequency-modulated FMCW transmitted signal.

According to a further embodiment, the transmitting wire is arranged on a circuit board fastened in the antenna.

According to a further embodiment, a compensation element, in particular a metal cone or a metal ring, is arranged on the transmitting wire.

According to a further embodiment, an insert made of a dielectric, in particular of polytetrafluoroethylene (PTFE), is arranged in the antenna and fills the space inside the antenna in the vicinity of the transmitting wire.

According to a further embodiment, the antenna has a first fastening device, in particular a flange or an external thread, by means of which it can be fastened at a location, in particular on a tank or a vessel.

Furthermore, the invention comprises the use of one of the abovementioned arrangements in a filling level measuring device.

One advantage is that the coupling in of the coaxial line into the antenna takes place at the rear wall of the latter. Consequently, the arrangement has a small outside diameter and can, for example, be fitted in small openings.

A further advantage of the invention is that the geometry of the arrangement makes it virtually impossible to induce the next-higher mode (TM-01) from the transmission mode. Although, in a frequency range dependent on the diameter of the antenna, both the desired TE-11 mode and the next-higher TM-01 mode would, in principle, be capable of propagation, a frequency range which is greater than the monomode range of the TE-11 mode can be used, since only the TE-11 mode is induced and the formation of the TM-01 mode is prevented by destructive interference of the same in the proximity of the transmitting wire.

The invention and further advantages are now explained in more detail with reference to the figures of the drawing, in which two exemplary embodiments of the arrangement for generating and transmitting microwaves and three exemplary embodiments of filling level measuring devices are represented; identical elements are provided with identical designations in the figures.

Figure 1:
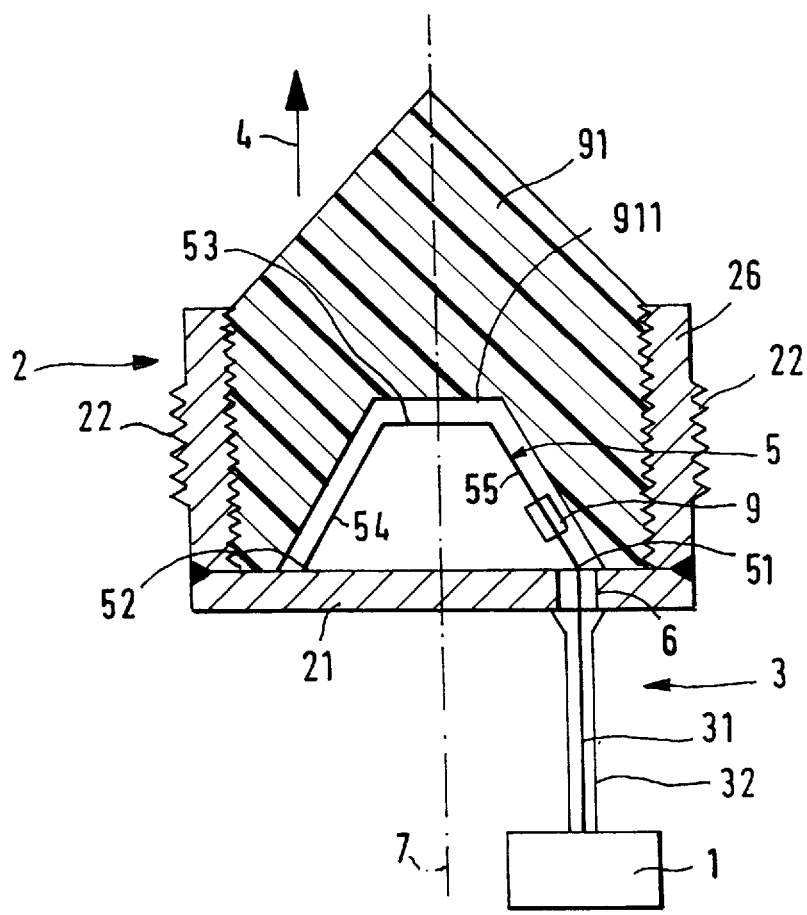
FIG. 1 shows diagrammatically an arrangement for generating and transmitting microwaves and a longitudinal section through an antenna with a transmitting wire.

In FIG. 1 there is diagrammatically represented an arrangement for generating and transmitting microwaves. The microwaves are generated by a microwave generator 1 and transmitted by means of an antenna 2.

The microwave generator 1 is, for example, a pulse radar device, an FMCW device or a continuously oscillating microwave oscillator.

A commercially available coaxial line 3 with an inner conductor 31 and an outer conductor 32 leads from the microwave generator 1 to the antenna 2.

The antenna consists of an electrically conducting material, for example aluminum or a high-grade steel, or of a plastic coated with a conductive material, and has a circular cross section. The radiating direction of the microwaves is indicated by the arrow 4.

The antenna 2 comprises a hollow cylinder 26 and a rear wall 21, closing off the hollow cylinder 26. The antenna 2 consequently has the geometry of a short-circuited circular waveguide.

In the antenna 2, a transmitting wire 5 of a conductive metal, for example copper, silver or aluminum, is arranged on the rear wall 21. A first end 51 of the transmitting wire 5 is connected electrically conductively to the inner conductor 31 of the coaxial line 3.

For this purpose, a lead-through 6, for example a glass lead-through, is provided in the rear wall 21. The lead-through 6 must have an insulation layer, in order to ensure that no electrically conducting connection between the inner conductor 31 and the rear wall 21 exists in the region of the lead-through 6. The outer conductor 32 of the coaxial line 3 is connected electrically conductively to the rear wall 21 of the antenna 2. The rear wall 21 assumes the function of an outer conductor in the case of this coaxial lead-through.

The second end 52 of the transmitting wire 5 is connected electrically conductively to the rear wall 21 of the antenna 2. For example, it is soldered onto the rear wall 21, or the rear wall 21 has a blind hole into which the transmitting wire 5 can be inserted, if appropriate with a fixing element interposed. The fixing element may be, for example, a metal sleeve or a plastic sleeve. The plastic sleeve is to be selected such that an electrically conducting connection exists between the transmitting wire 5 and the rear wall 21 for the desired frequency range of the microwaves. There is then a capacitive connection of the transmitting wire 5 to the rear wall 21, i.e. an electrically conducting connection exists for microwaves, but the plastic sleeve acts as an insulator for low-frequency currents and for DC voltage.

Figure 2:
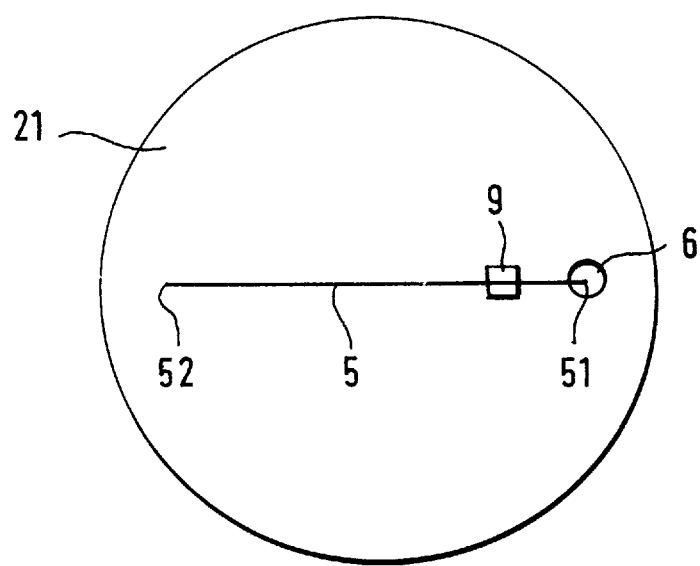
FIG. 2 shows a plan view of the side of the rear wall of the antenna, on which the transmitting wire is arranged.

Apart from the two ends 51, 52, which are, as already described, arranged on the rear wall 21 of the antenna 2, the transmitting wire 5 runs in the interior of the antenna 2, as can be seen from FIGS. 1 and 2. The transmitting wire 5 has three regions, a straight portion 53, running at a distance from the rear wall 21 of the antenna 2, and two legs 54, 55, adjoining said straight portion and leading from the latter to the ends 51 and 52, respectively. These legs 54, 55 are inclined with respect to the longitudinal axis 7 of the antenna 2, so that the distance between the hollow cylinder 26 of the antenna 2 and the legs 54, 55 increases with increasing distance from the rear wall 21 of the antenna 2.

To achieve as high a microwave transmission power as possible at a single predetermined transmission frequency, the geometry of the transmitting wire 5 is to be chosen such that the area of intersection bounded by the transmitting wire 5 and the rear wall 21 of the antenna 2 is trapezoidal and is arranged symmetrically with respect to the longitudinal axis 7. This highly symmetrical geometry of the transmitting wire 5 brings about an optimum adaptation of the electrical impedance for the predetermined frequency. Furthermore, the symmetry of the arrangement prevents the inducement of the next-higher, asymmetric TM-01 mode.

However, in order for the average microwave transmission power to be as great as possible over a predetermined frequency range, it is necessary to depart from this highly symmetrical geometry. For example, the legs 54, 55 are to be arranged in such a way that they are inclined to different extents with respect to the longitudinal axis and/or the straight portion 53 is to be arranged inclined with respect to the rear wall 21 instead of parallel to it. Instead of an optimum adaptation for a single frequency, there is consequently a good adaptation for a frequency range.

With a departure from the highly symmetrical geometry specified above, it is admittedly not possible to prevent the TM-01 mode from being generated, but it is already suppressed by destructive interference in the proximity of the transmitting wire 5. This is caused by the division of the transmitting wire 5 into three regions, to be specific the portion 53 and the legs 54, 55 and their geometrical arrangement in the antenna 2.

The optimum form of the transmitting wire 5 for an antenna 2 with a predetermined diameter can be determined either experimentally, or be computationally established by approximation solutions of Maxwell's equations, including all boundary conditions, such as the dimensions and material of the antenna 2, the material of the transmitting wire 5 and the frequency range.

The desired microwave mode is induced primarily by the portion 53 of the transmitting wire 5 running in the interior of the antenna 2. For generating the desired TE-11 mode, the average distance between the portion 53 of the transmitting wire 5 and the rear wall 21 of the antenna 2 must be chosen such that it is equal to one quarter of the waveguide wavelength $\lambda_H$ of the TE-11 mode in the circular waveguide antenna 2. For the determination of this waveguide wavelength $\lambda_H$, a relevant frequency of the microwaves to be transmitted must be used. If using a pulse radar generator, the relevant frequency is equal to a center frequency of a frequency spectrum of the transmission pulse and, if using a linearly frequency-modulated FMCW generator, it is equal to the center frequency of the latter.

In the case of the arrangement described, it is possible to allow a frequency range for the microwaves which is greater than the frequency range in which, with given dimensions, the TE-11 mode alone is capable of propagation, without the next-higher TM-01 mode being generated and transmitted.

In the case of an antenna 2 with a diameter of 25 millimeters, having an insert 91 which is described in more detail in the text which follows and is made of a dielectric with a dielectric constant of 2.0, the cutoff frequency for the TE-11 mode is 5.0 GHz and for the TM-01 mode is 6.5 GHz. Below its cutoff frequency, the respective mode is not capable of propagation. The frequency range in which only the TE-11 mode is capable of propagation has a bandwidth of 6.5 GHz–5.0 GHz=1.5 GHz. The arrangement according to the invention can be used, however, up to frequencies of 7.2 GHz, without the TM-01 mode being produced; this corresponds to a bandwidth of 7.2 GHz–5.0 GHz=2.2 GHz and consequently a widening of the usable frequency bandwidth of 2.2 GHz/1.5 GHz=146%.

Instead of a transmitting wire 5 running freely in the antenna 2, fastened only at its ends 51, 52, a circuit board 8 on which a corresponding transmitting wire 5 is arranged can also be used. This is diagrammatically represented in FIGS. 3 and 4. For fastening the circuit board 8, there may be a groove arranged in the rear wall 21, lying along the diagonal, and two grooves arranged in the hollow cylinder 26, lying diametrically opposite each other, into which grooves the circuit board 8 can be inserted. The electrical contacting of the ends 51 and 52 of the transmitting wire 5 is performed in a way analogous to the contacting of the transmitting wire 5 without circuit board 8.

The circuit board 8 has an influence on the propagation of the microwaves in the region of the antenna 2. Particularly the edge 81 of the circuit board 8, which points in the radiating direction, represents a sudden change in impedance. In order to keep down power loss caused as a result, it is recommendable to use instead of a rectangular circuit board a circuit board 8 which has a width which narrows in the radiating direction, for example triangularly, represented in FIG. 3. This achieves a continuous matching of the impedance.

A further sudden change in impedance occurs at the transition from the coaxial line 3 to the transmitting wire 5 in the antenna 2. In order also to keep down losses caused as a result, on the one hand there is provided a compensation element 9, which is arranged at the region of the leg 55 of the transmitting wire 5 adjoining the lead-through 6. In the exemplary embodiment shown, this is a metal ring. Other components which change the characteristic impedance of transmitting wire 5, for example a metal cone, can be used. On the other hand, the increase in the distance between the hollow cylinder 26 of the antenna 2 and the legs 54, 55 with increasing distance from the rear wall 21 of the antenna 2 brings about a continuous transition of the impedance to the impedance of the antenna.

For the continuous adaptation of the impedance of the antenna 2 to the impedance of the outer space, into which the microwaves are to be transmitted, in the antenna 2 there may be arranged an insert 91 which is made of a dielectric, in particular polytetrafluoroethylene (PTFE), and is shown in FIG. 1. This insert has a cylindrical portion, which completely fills the space inside the antenna, apart from the space required for the transmitting wire 5 and, if appropriate the circuit board 8, and a conical portion, which protrudes out of the antenna 2 and the tip of which points in the radiating direction. This insert 91 is fastened, for example, by having an external thread 92, which can be screwed into an internal thread arranged in the hollow cylinder 26. Subsequently, the rear wall 21, with the transmitting wire 5 arranged on it, is mounted on the hollow cylinder 26, for example welded on. For receiving the wire 5, the insert 91 has a recess 911. Other methods of fastening, for example by means of a peripheral shoulder which is arranged on the inside wall of the hollow cylinder 26 and prevents movement of the insert 91 in the radiating direction, are of course possible.

The antenna 2 has a first fastening device, by means of the arrangement can be fastened at a location, for example on a tank or vessel. This device is, for example, a flange, or, as shown in FIG. 1, an external thread 22.

Also provided on the antenna 24 on the rear wall 21 is a second fastening device, by which a housing can be fastened. For example, the housing is screwed onto an external thread integrally formed on the antenna 2. It is advantageous here that, because the microwaves are coupled in through the rear wall 21, there is no additional space requirement for this. The inside diameter of the housing corresponds to the outside diameter of the antenna 2.

The arrangements described for generating and transmitting are suitable in particular for filling level measurement, since they permit the low-loss transmission of microwaves or microwave pulses at frequencies of one bandwidth. Known methods of filling level measurement by means of microwaves have already been mentioned in the introduction. As far as the mechanical construction is concerned, reference is made to FIGS. 1 to 4 and their description.

Microwave radiation impinging on the antenna is conducted by it onto the transmitting wire 5. An echo signal reflected from the surface of the filled product consequently passes via the transmitting wire 5, then serving as a receiving wire, to the coaxial line 3 and is available, for example by interposing a directional coupler, for further processing and/or evaluation.

Figure 3:
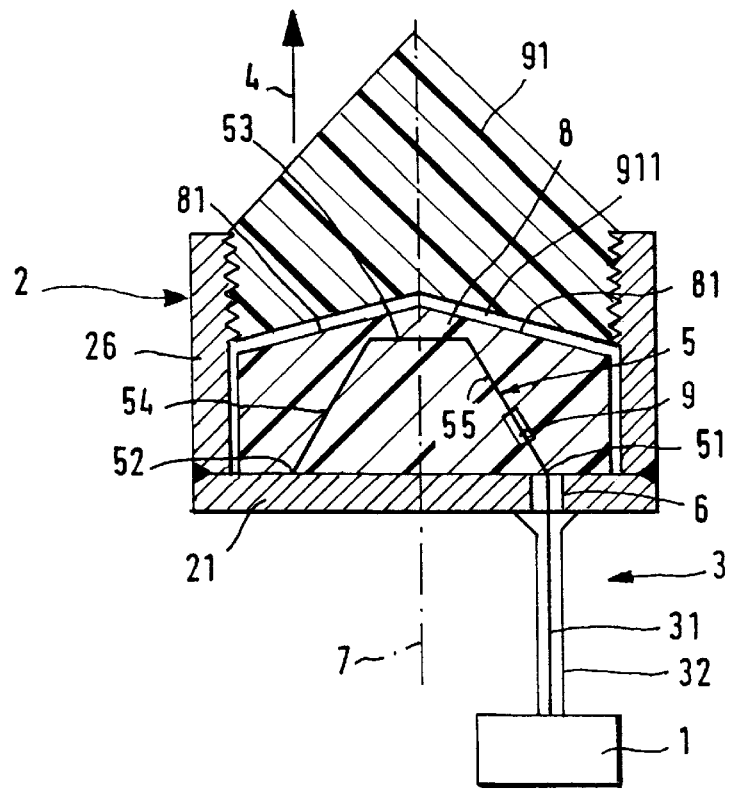
FIG. 3 shows diagrammatically an arrangement for generating and transmitting microwaves and a longitudinal section through an antenna, in which the transmitting wire is arranged on a circuit board.
Figure 4:
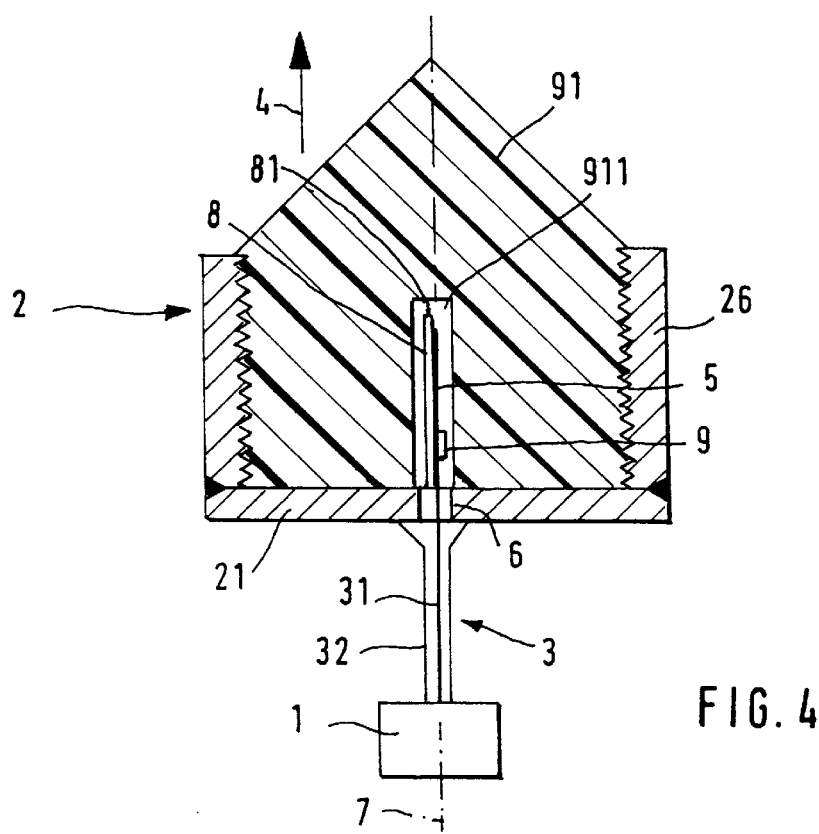
FIG. 4 shows the arrangement from FIG. 3, turned through 90°.
Figure 5:
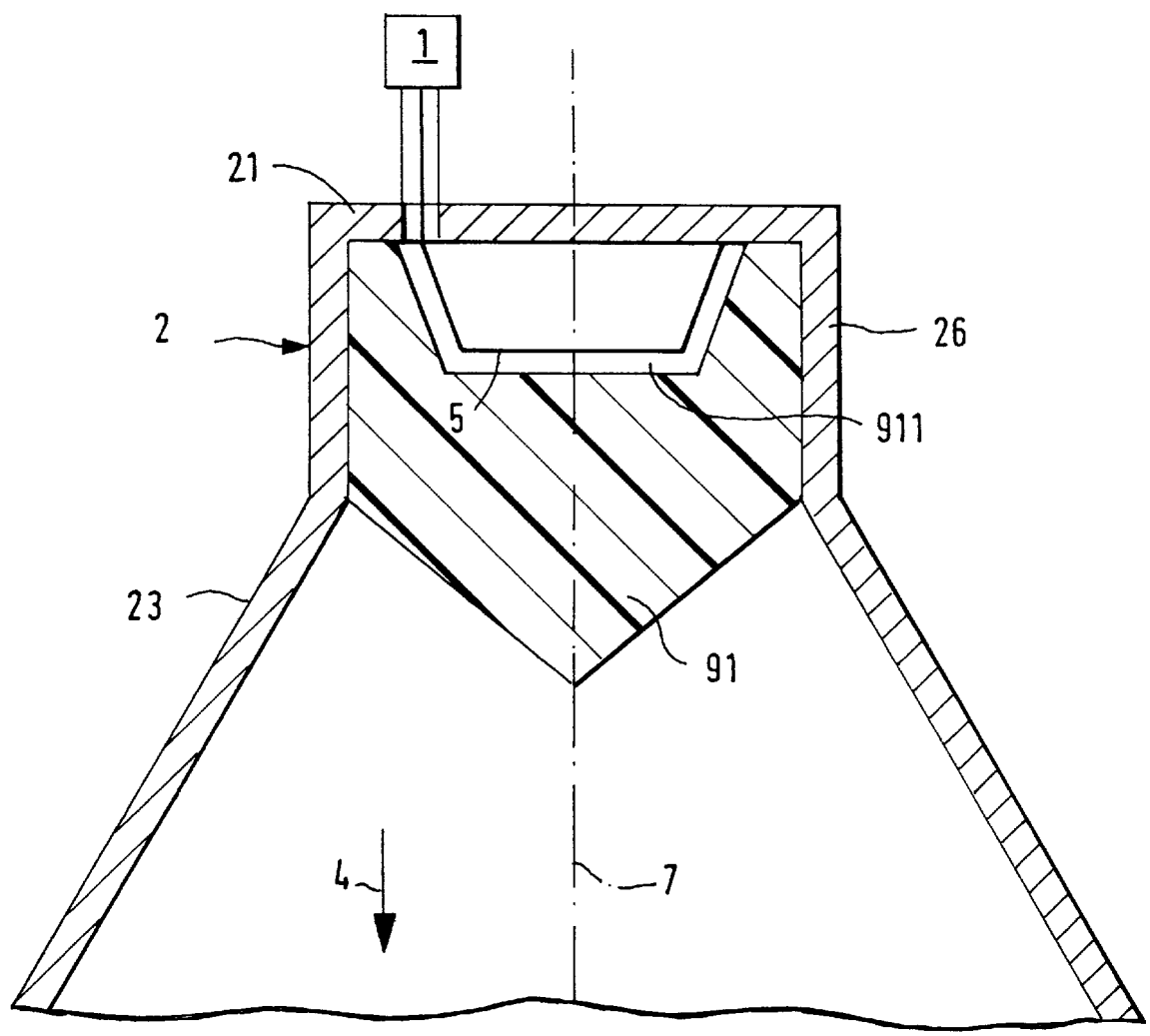
FIG. 5 shows a diagrammatical representation of a filling level measuring device with a horn radiator.
Figure 6:
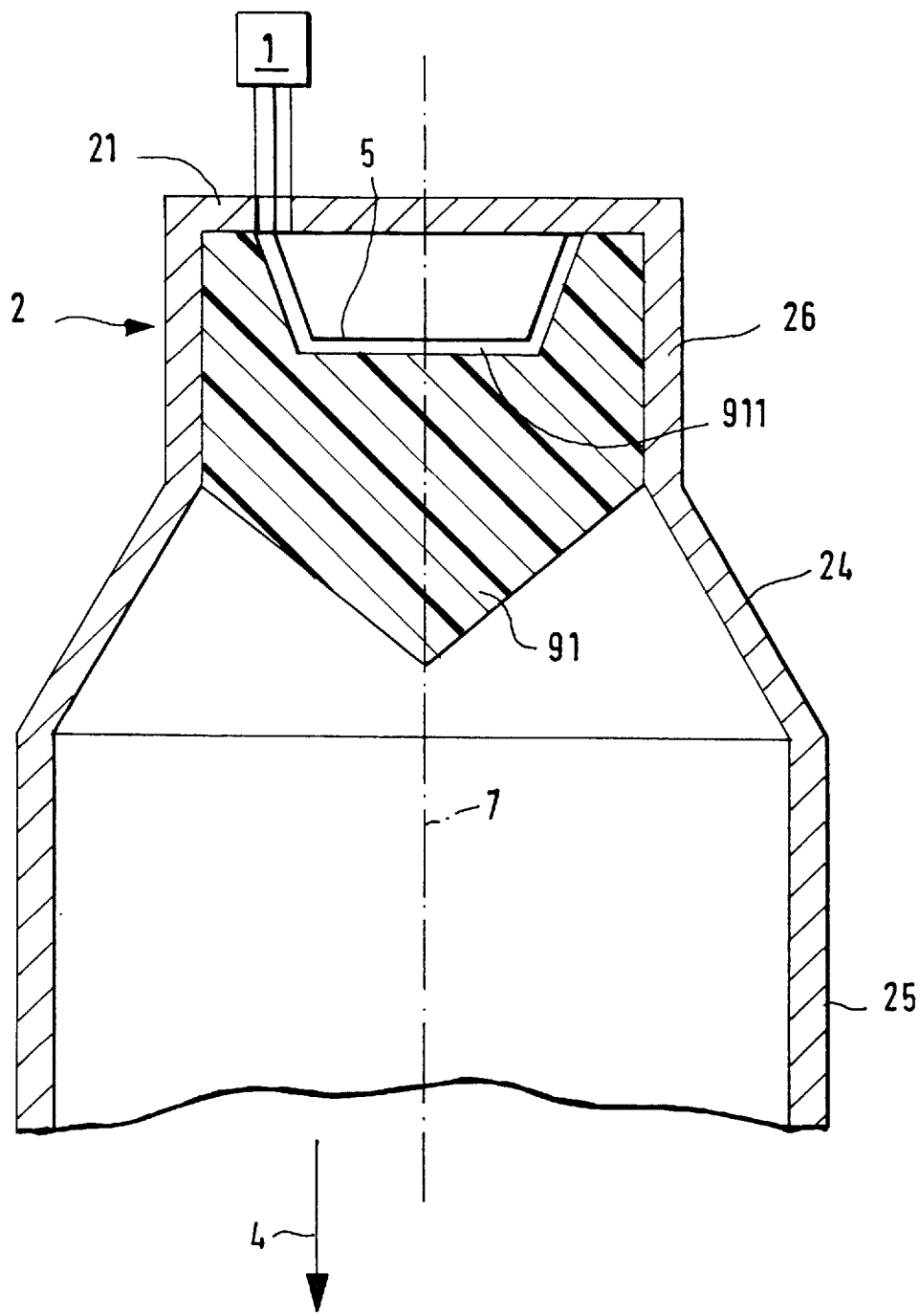
FIG. 6 shows a diagrammatical representation of a filling level measuring device, which is arranged on a surge pipe or bypass pipe.
Figure 7:
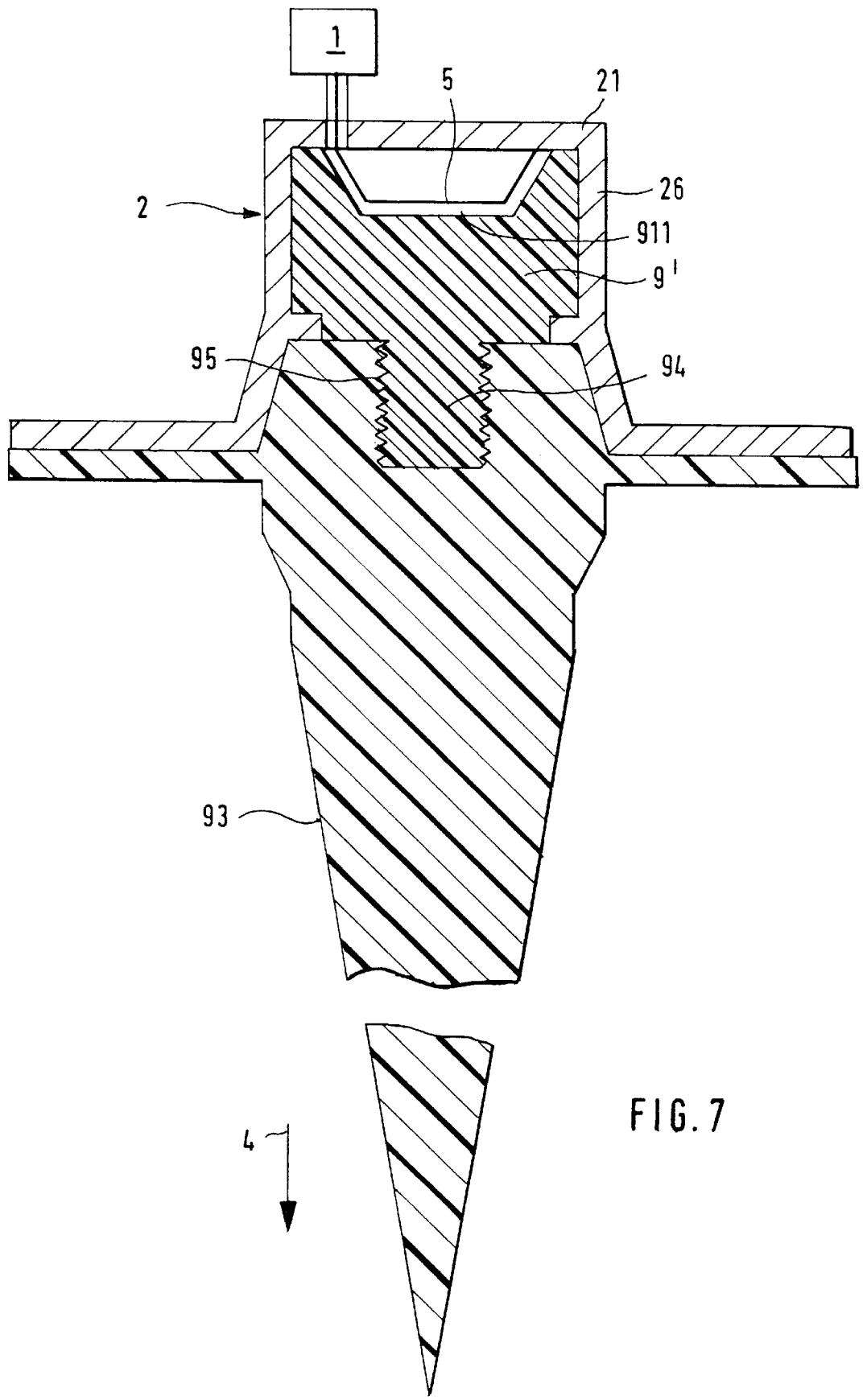
FIG. 7 shows a diagrammatical representation of a filling level measuring device with a rod antenna.

The arrangements represented in FIGS. 1 to 4 can be provided directly, without any modifications, with the types of antenna customary in filling level measuring technology. FIGS. 5 to 7 show a number of examples, which are just diagrammatically represented.

The filling level measuring device represented in FIG. 5 has an arrangement for generating and transmitting microwaves, as it is represented for example in FIG. 1 or FIG. 3. Integrally formed onto the antenna 2 is a funnel 23. Antenna 2 and funnel 23 form a horn radiator. The rear wall 21 is adjoined, for example, by a housing (not shown here), in which the microwave generator 1, the coaxial line 3 and evaluation electronics are arranged.

FIG. 6 shows an arrangement corresponding to FIG. 1 or 3, in which the antenna 2 is arranged on a surge pipe or bypass pipe 25, via an adaptation element 24.

The filling level measuring device represented in FIG. 7 has a rod antenna 93 made of a dielectric, for example of polytetrafluoroethylene (PTFE). For this purpose, instead of the insert 91 represented in FIGS. 1 and 3, with a conical portion, a cylindrical insert 9' is used, a cylindrical portion 94 with an external thread 95 being integrally formed onto the front face thereof, pointing in the radiating direction. Screwed onto this external thread is the rod antenna 93, which has an identically shaped recess with an internal thread.

I claim:

1. An arrangement for generating and transmitting microwaves, having
   a microwave generator (1),
   an antenna (2) of circular cross section and
   a coaxial line (3) leading from the microwave generator (1) to the antenna (2), having an inner conductor (31) and an outer conductor (32),
   wherein
   there is fastened on the rear wall (21) of the antenna (2) a transmitting wire (5),
   which runs in the interior of the antenna (2),
   the first end (51) of which is connected to the inner conductor (31) of the coaxial conductor (3),
   the second end (52) of which is connected to the rear wall (21) of the antenna (2) and
   which has a straight portion (53) and two legs (54, 55) adjoining the latter.

2. The arrangement as claimed in claim 1, wherein
   the straight portion (53) of the transmitting wire (5) runs at a distance from the rear wall (21) of the antenna (2) and
   the distance between the antenna (2) and two legs (54, 55) of the transmitting wire (5), which are bounded by the ends (51, 52) and the portion (53), increases with increasing distance from the rear wall (21) of the antenna (2).

3. The arrangement as claimed in claim 2, wherein the average distance between the straight portion (53) of the transmitting wire (5) and the antenna (2) is equal to one quarter of the waveguide wavelength ($\lambda_H$) in the antenna (2) at a frequency to be transmitted, in particular at a center frequency of a frequency spectrum of a microwave transmission pulse to be transmitted or at a center frequency of a linearly frequency-modulated FMCW transmitted signal.

4. The use of an arrangement as claimed in claim 3 in a filling level measuring device.

5. The use of an arrangement as claimed in claim 2 in a filling level measuring device.

6. The arrangement as claimed in claim 1, wherein the transmitting wire (5) is arranged on a circuit board (8) fastened in the antenna (2).

7. The use of an arrangement as claimed in claim 6 in a filling level measuring device.

8. The arrangement as claimed in claim 1, wherein a compensation element (9), in particular a metal cone or a metal ring, is arranged on the transmitting wire (5).

9. The use of an arrangement as claimed in claim 8 in a filling level measuring device.

10. The arrangement as claimed in claim 1, wherein an insert made of a dielectric, in particular of polytetrafluoroethylene (PTFE), is arranged in the antenna (2) and fills the space inside the antenna in the vicinity of the transmitting wire (5).

11. The use of an arrangement as claimed in claim 10 in a filling level measuring device.

12. The arrangement as claimed in claim 1, wherein the antenna (2) has a first fastening device, in particular a flange or an external thread (22), by means of which it can be fastened at a location, in particular on a tank or a vessel.

13. The use of an arrangement as claimed in claim 12 in a filling level measuring device.

14. The use of an arrangement as claimed in claim 1 in a filling level measuring device.

* * * * *